United States Patent [19]

Hutson

[11] Patent Number: 5,662,109
[45] Date of Patent: Sep. 2, 1997

[54] METHOD AND SYSTEM FOR MULTI-DIMENSIONAL IMAGING AND ANALYSIS FOR EARLY DETECTION OF DISEASED TISSUE

[76] Inventor: William H. Hutson, 47 Grange St., Little Compton, R.I. 02837

[21] Appl. No.: 422,031

[22] Filed: Apr. 14, 1995

Related U.S. Application Data

[63] Continuation-in-part of Ser. No. 367,787, Dec. 30, 1994, Pat. No. 5,455,806, which is a continuation of Ser. No. 119,362, Sep. 10, 1993, Pat. No. 5,379,268, which is a continuation of Ser. No. 978,245, Nov. 18, 1992, Pat. No. 5,245,587, which is a continuation-in-part of Ser. No. 628,337, Dec. 14, 1990, Pat. No. 5,175,710.

[51] Int. Cl.⁶ .................................................... A61B 8/00
[52] U.S. Cl. ............................... 128/653.1; 128/653.2
[58] Field of Search ............................. 128/653.1, 653.2, 128/660.09, 915, 662.06, 661.08

[56] References Cited

U.S. PATENT DOCUMENTS

| | | | |
|---|---|---|---|
| 4,651,744 | 3/1987 | Bristow et al. | 128/660 |
| 5,099,846 | 3/1992 | Hardy | 128/653.1 |
| 5,348,020 | 9/1994 | Hutson | 128/696 |
| 5,479,927 | 1/1996 | Shmulewitz | 128/660.09 |

FOREIGN PATENT DOCUMENTS

| | | |
|---|---|---|
| 4309597 | 9/1994 | Germany . |
| 9511627 | 5/1995 | WIPO . |

*Primary Examiner*—Marvin M. Lateef
*Assistant Examiner*—Derrick Fields
*Attorney, Agent, or Firm*—Hale and Dorr LLP

[57] ABSTRACT

An enhancer receives, combines, and correlates at least two sets of data from different imaging sources, such as a mammographic imaging system and an ultrasound imaging system, for imaging bodily tissue, such as breast tissue. The processed data can then be displayed. The enhancer embeds sets of data in matrixes and uses singular value decomposition to compress the data into singular vectors and singular values. The compressed data can be altered to enhance or suppress desired features.

14 Claims, 5 Drawing Sheets

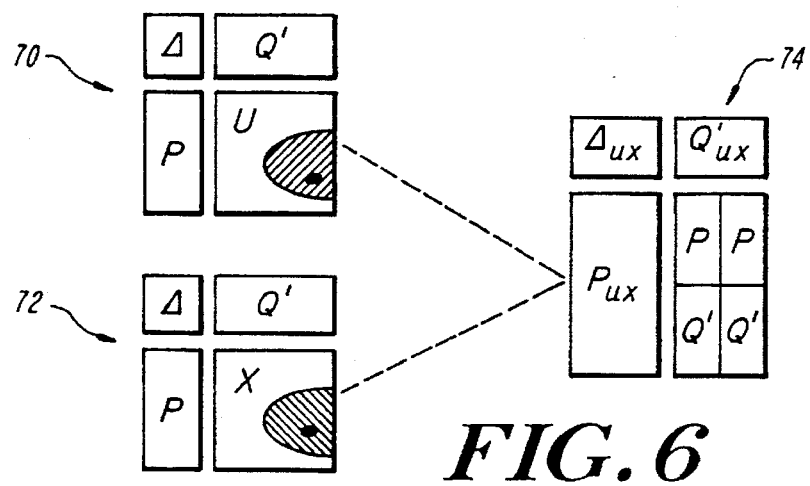
*FIG. 6*
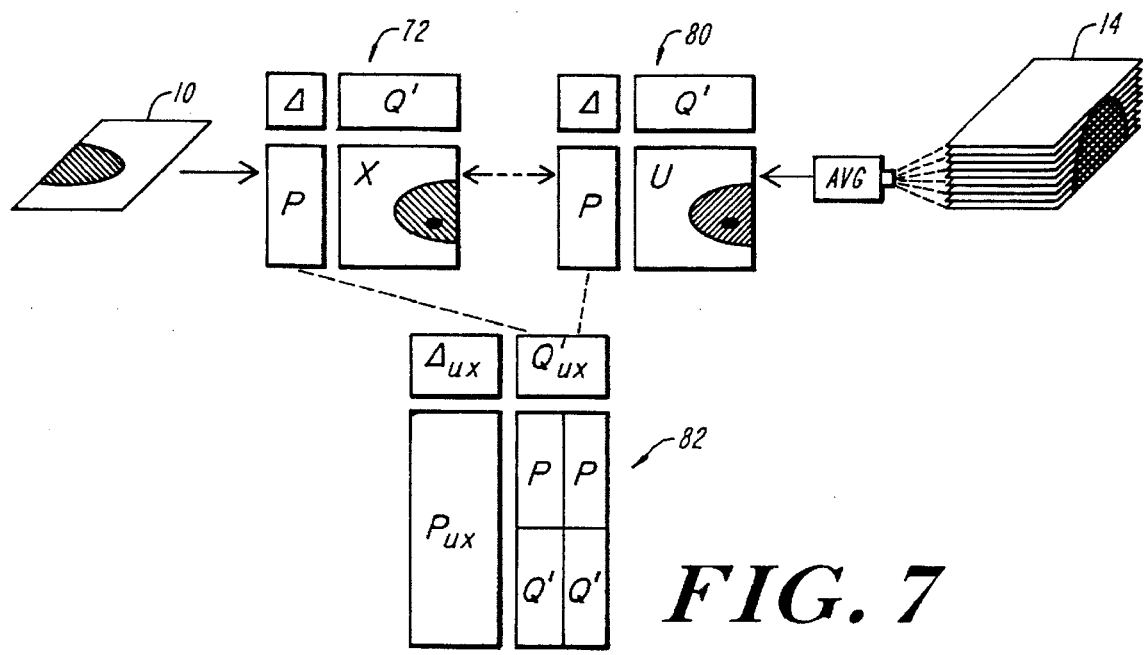
*FIG. 7*
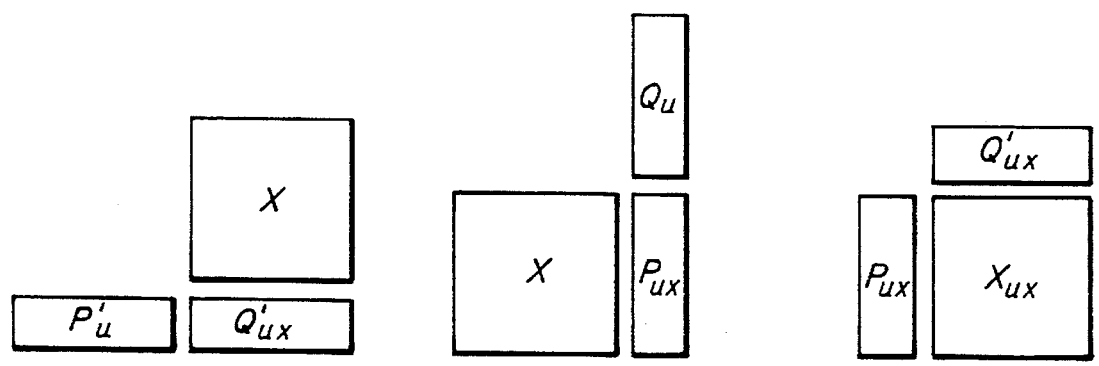
*FIG. 8A*   *FIG. 8B*   *FIG. 8C*

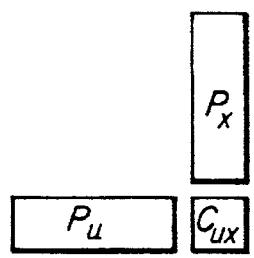 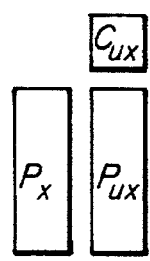 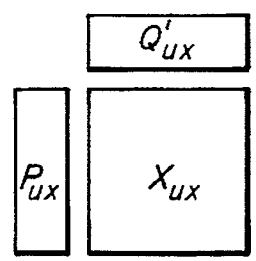
FIG. 9A  FIG. 9B  FIG. 9C
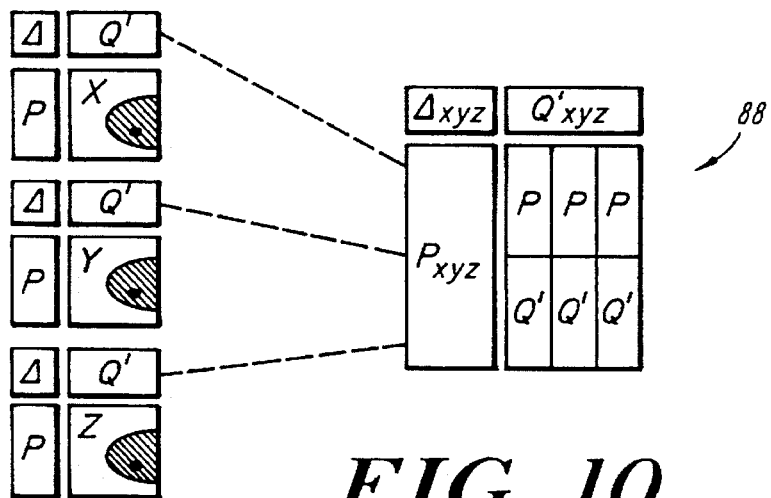
FIG. 10
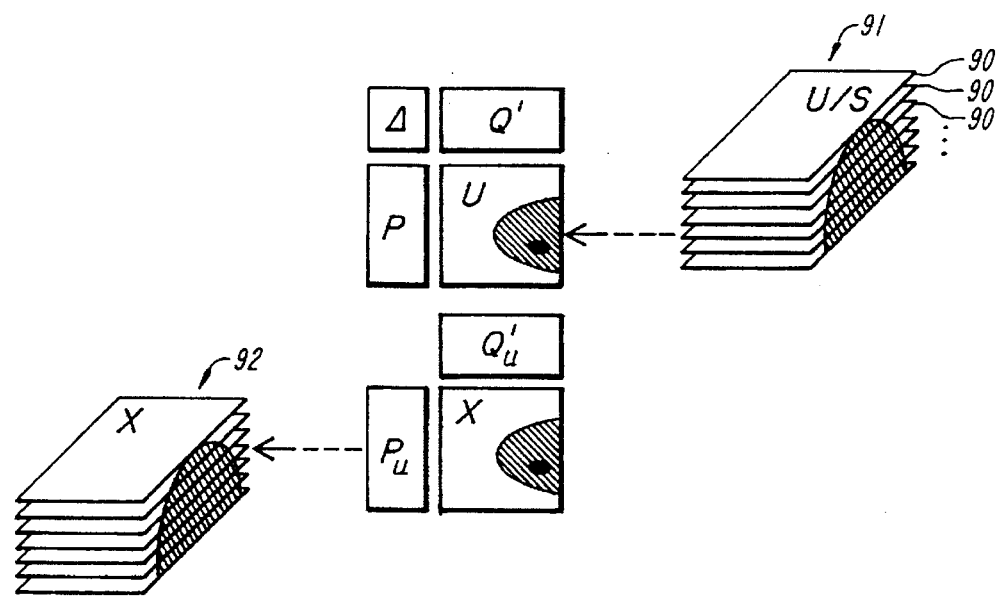
FIG. 11

METHOD AND SYSTEM FOR MULTI-DIMENSIONAL IMAGING AND ANALYSIS FOR EARLY DETECTION OF DISEASED TISSUE

CROSS REFERENCE TO RELATED APPLICATIONS

This application is a continuation-in-part of U.S. Ser No. 08/367,787, filed Dec. 30, 1994, now U.S. Pat. No. 5,455, 806 which is a continuation of U.S. Ser. No. 08/119,362 filed Sep. 10, 1993, now U.S. Pat. No. 5,379,268, which is a continuation of U.S. Ser. No. 07/978,245, filed Nov. 18, 1992, now U.S. Pat. No. 5,245,587, which is a continuation-in-part of U.S. Ser. No. 07/628,337, filed Dec. 14, 1990, now U.S. Pat. No. 5,175,710.

FIELD OF THE INVENTION

This invention generally relates to systems and methods for the diagnostic imaging of bodily tissue for the early detection of structural abnormalities and carcinomas. More specifically, it relates to systems and methods for early detection of diseased tissue using a plurality of modalities.

BACKGROUND OF THE INVENTION

Currently, bodily tissues can be imaged in a number of different ways, including radiation, ultrasound, and magnetic resonance imaging (MRI). These methods have different benefits and drawbacks in terms of cost and accuracy.

One important application of the imaging of bodily tissue is the screening of breast tissue for the early detection of breast lesions and carcinoma. The primary tool for such imaging is mammography, which involves a low-dose radiographic imaging of breast tissue structures. Mammographic imaging works best when breast tissue is radiologically differentiated, i.e., when there is good contrast between ductal, lobular, nodal, and fatty tissue types. Because breast tissue becomes more differentiated as a woman matures, mammography tends to work better on older patients than for younger patients, whose breast tissue is more dense and whose tissue types are not yet as radiologically differentiated. Mammography also does not work well on patients who have had breast augmentation, such as breast implants, or on patients who have had breast surgery, including lumpectomies or mastectomies. Another problem is present-day mammography machines do not image all of the breast tissue. Specifically, breast tissue close to the thoracic wall generally is not within the field of view of mammograms, so diseased lymph nodes in this area will not be diagnosed early. Moreover, there are also concerns about variations in the quality; reproducibility, and resolution of mammographic imaging. A yet further problem with mammography is that it has a high rate of producing false-positives, i.e., indications that suspect tissue masses are malignant that turn out to be benign after further testing; and even more critically, a high rate of false-negatives, i.e., malignant tissue misdiagnosed as nonmalignant.

Despite these limitations, mammography is still regularly used because it remains the easiest method for the early detection of carcinomas without considerable time, effort, and cost. Furthermore, it can detect some non-palpable carcinomas that may have been otherwise missed, and can sometimes help rule out benign palpable masses.

There is a need for a system and method to provide better imaging of tissues, and particularly for a system and method for providing reliable early detection of breast carcinomas or other diseased tissue without a high number of false-positives and false-negatives.

SUMMARY OF THE INVENTION

The present invention is a system and method for imaging bodily tissues. The system and method enable reliable early detection of carcinomas in bodily tissue, more complete coverage of bodily tissue, and a reduction in the number of false-positives and false-negatives in the diagnosis of diseased tissues, such as carcinomas.

The system combines and correlates sets of data produced from images obtained through different modalities, such as ultrasound, mammography, magnetic resonance imaging (MRI), and single position emission tomography (SPECT), to provide a set of output data that can be analyzed. While the system is described herein primarily in connection with the imaging of breasts through use of mammographic imaging and ultrasound imaging, it can be used with many different imaging methods for imaging different types of bodily tissues.

According to one embodiment of the present invention, data from mammographic imaging is enhanced with data from ultrasonic imaging to produce a reproducible, full-breast, three-dimensional image that may be stored, retrieved, and compared with subsequent diagnoses. The system reduces noise and interference from medical imagery, allows features of interest to be enhanced, and allows other features to be suppressed. By combining mammographic imaging with other modalities, such as ultrasound, and by enhancing the reliable determination of specific bodily tissue structures, the amount of unnecessary fine-needle aspirations, biopsies, and histological studies in patients with benign cysts can be reduced.

In a preferred embodiment, the system receives a set of data representing a two-dimensional mammographic image, and a set of three-dimensional ultrasound data, arranged as a series of two-dimensional sets of data. Each set of two-dimensional data may be represented by a two-dimensional matrix, which is compressed by decomposing it using singular value decomposition (SVD), eigenvector decomposition (EVD), or other suitable means, such as disclosed, for example, in U.S. Pat. Nos. 5,348,020 and 5,245,587. The decomposed data from the plurality of modalities is correlated and combined into a new matrix that is then decomposed using SVD, EVD, or other suitable means into left singular vectors, singular values, and right singular vectors in various combinations of dimensions. The data can also be selectively enhanced or suppressed in order to emphasize or suppress selected features. For the series of two-dimensional data provided from the ultrasound, the data is preferably concatenated into a single matrix or, alternatively, the ultrasound data can be averaged to form a single two-dimensional matrix of smaller dimensions. While the above description relates to a single set of two-dimensional mammographic data and multiple sets of two-dimensional ultrasound data, the system and method of the present invention can be used with multiple sets of data.

BRIEF DESCRIPTION OF THE DRAWINGS

FIG. 6 illustrates data fusion of two two-dimensional images according to the present invention.

FIG. 7 illustrates the data fusion of a first set of two-dimensional images and a second set of two-dimensional images according to an alternative embodiment of the present invention.

FIGS. 8(a)–8(c) and 9(a)–9(c) are representations of matrices illustrating alternative ways for correlating different sets of data.

FIGS. 10–12 illustrate further embodiments of data fusion according to the present invention.

DETAILED DESCRIPTION

The present invention relates to the imaging of bodily tissues, and particularly to a system and method for enabling early detection of carcinomas and other types of diseased bodily tissue. The system and method of the present invention correlate data from multiple modalities for medical imaging, including, mammography and other radiological procedures, ultrasound imaging, including pulsed and CW doppler, MRI, MRI spectroscopy (MRIS), fluoroscopy, angiography, computer tomography (CT), ultrafast computer tomography (UFCT), electrocardiography (EKG), echocardiography (ECG), electroencephalography (EEG), positron emission tomography (PET), single positron emission tomography (SPECT) and other medical sensing systems. Through the intracorrelation and intercorrelation of multiple modalities, more effective use can be made of these techniques.

The system of the present invention preferably operates in near realtime. It processes data signals from medical imaging equipment to produce an image having two or more dimensions, shows important characteristics within the data, and allows for the suppression of certain characteristics and the enhancement of other characteristics. The system compresses detected data for further processing and enhancement, and allows the compressed data (or compressed and enhanced data) to be transmitted to remote locations and to be reproduced at another time.

Figure 1:
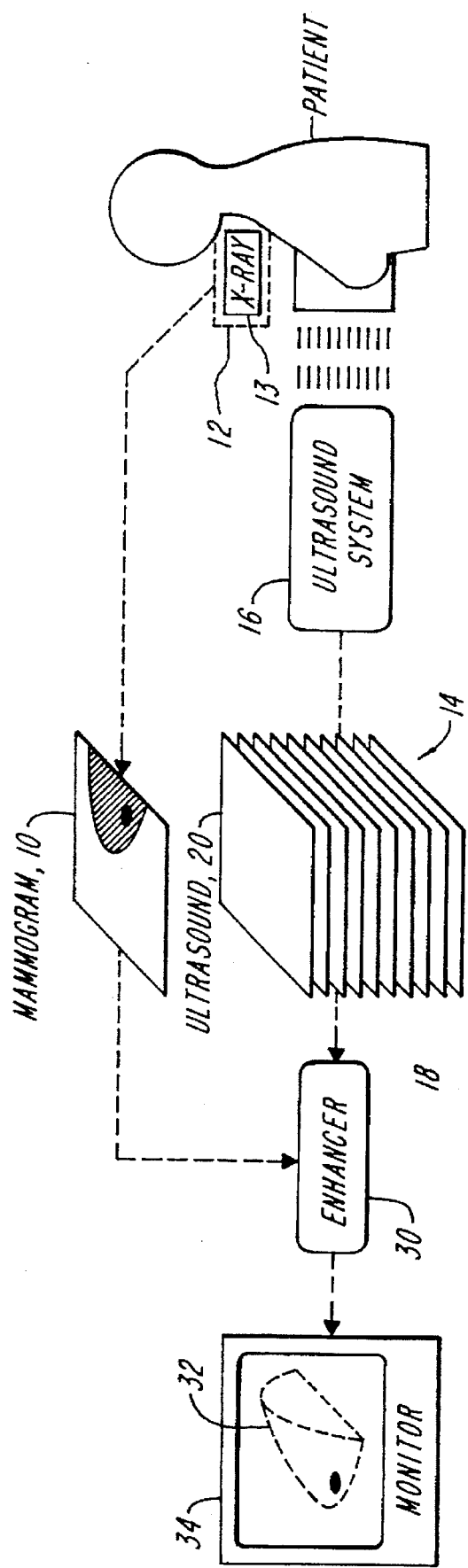
FIG. 1 shows the system and method for data enhancement and display according to the present invention.

Referring to FIG. 1, a patient's breast is imaged in such a way that two sets of data are provided: mammographic data 10 derived from mammographic imaging system 12, and ultrasound data 14 derived from an ultrasound imaging system 16. A typical full-breast ultrasound imaging system records high frequency ultrasound energy that reflects off structures within a patient's breast. The ultrasound data may be produced from pulsed acoustic energy for high-resolution details of structures within the breast, or from continuous wave acoustic energy for doppler measurements of blood flow within the breast tissue. Ultrasound data 14 is generated as multiple levels 18 of two-dimensional images 20 of the breast tissue, thus yielding a three-dimensional data set. In contrast, mammographic data 10, produced with x-ray 13, is a two-dimensional composite of radiographic densities from different levels in the breast.

The three-dimensional ultrasound data and the two-dimensional mammographic data are input to enhancer 30, which receives the data and enables the three-dimensional representation 32 to be displayed on a monitor 34. Enhancer 30 may be integrated into ultrasound system 16 and/or mammographic imaging system 12, or it can be a stand-alone device that accepts data from these and other units. The enhancer of the present invention can be designed for a particular application, such as for combining only mammographic data and ultrasound data, or can be structured to flexibly work with many different combinations of imaging systems. The enhancer also may be provided as dedicated hardware, or preferably as a combination of hardware and software with the ability to perform the necessary calculations.

Figure 2:
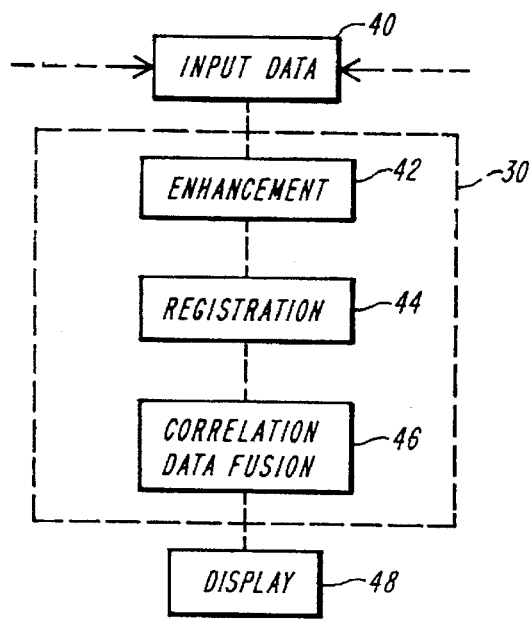
FIG. 2 shows the enhancer of the present invention in greater detail.

Referring also to FIG. 2, the steps of the method of the present invention are shown. According to this method, input data 40 from the two modalities is provided to enhancer 30. Enhancer 30 includes enhancement module 42 for carrying out step the enhancement step, registration module 44 for carrying out the registration step, and correlation and data fusion module 46 for integrating the two sets of data.

Input data 40 is received by enhancement module 42. This module weights, reformats, compresses, and enhances input data 40. Compression and enhancement, preferably, are performed with singular value decomposition (SVD), a well known technique described in more detail in the patents noted above. The resulting compressed and enhanced data is provided to the registration module 44.

The registration module expands and/or reduces selected dimensions of the resulting data to properly register and align the ultrasound and mammographic images for further processing. The registered images are then provided to correlation and data fusion module 46. This module correlates and enhances the different sets of data. The correlated and enhanced data is provided to display 48, such as monitor 34, so that the data can be viewed, interpreted, and analyzed. However, it is within the scope of the present invention that the registration step may occur before the compression step.

Figure 3:
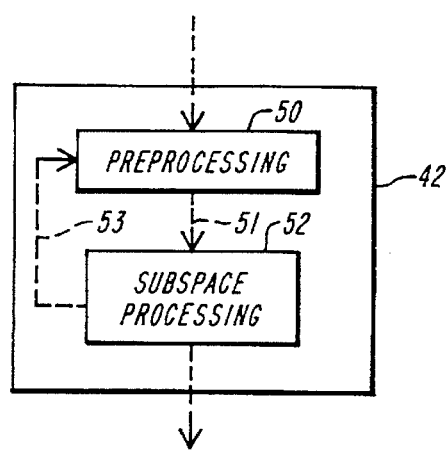
FIG. 3 shows the method steps of the enhancer shown in FIG. 2.

Referring to FIG. 3, when enhancement module 42 receives the input data such data is input to pre-processing module 50. Preprocessing module weights, reformats, and embeds the input data in two-dimensional matrix 51 shown in FIG. 4.

Figure 4:
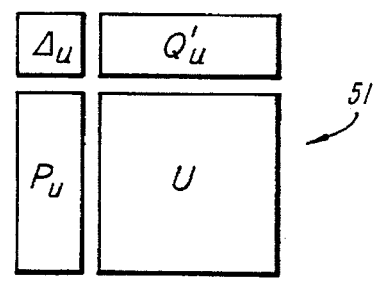
FIG. 4 is a representation of a matrix decomposed using SVD.

Referring to FIG. 4, matrix 51 is input to subspace processing module 52. This module compresses and enhances the two-dimensional matrix using SVD. More specifically, the data is decomposed into its left singular vectors P, its singular using singular values and singular vectors is well known in the prior art, as is matrix values A, and its fight singular vectors Q. The upper and lower case U and X in the figures relate to ultrasound data and mammographic data, respectively. Matrix analysis using eigenvalues and eigenvectors of the cross product of the input data. The compressed data is enhanced by selecting and modifying a subset of singular vectors and/or singular values. As the compressed and enhanced data is output from subspace processing module 52, it is also fed back to via line 53 to pre-processing module 50. This feedback data will be concatenated and combined with new input data.

Referring again to FIG. 2, the resulting compressed and enhanced data that are fed into registration module 44 are aligned, i.e., registered, by expanding or reducing the dimensions of one data set relative to the other. For example, the registration module may cause the outer boundaries of the breast to be at the same location for two modalities even in light of one modality providing more data between the same outer boundaries.

Figure 5:
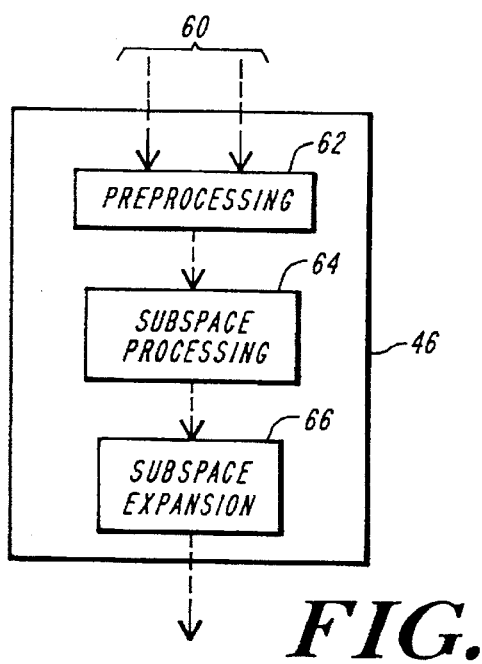
FIG. 5 shows the method steps of the system element for performing the correlation and data fusion step shown in FIG. 2.

Referring to FIG. 2 and 5, following data registration, the compressed, enhanced, and aligned data 60 is input to correlation and data fusion module 46. Data 60 is received by pre-processing module 62 and in subspace processing module 64, data from the one or more modalities is correlated and combined. Referring also to FIG. 6, in one embodiment of the present invention, data 60 consists of two sets of singular vectors P and Q' corresponding to ultrasonic data U and mammographic data X. These sets of vectors, 70 and 72, are weighted and concatenated to form a new matrix 74.

Referring to FIG. 7, in contrast to the embodiment shown in FIG. 6, ultrasound data 14 may be aligned, arranged, and compressed to produce a single set of two-dimensional averaged ultrasound data 80. This data is then combined with mammographic data 72 to form new matrix 82.

Under either embodiment, the resulting matrix data is then input to subspace processing module 64. At this module the concatenated singular vectors are decomposed, preferably through SVD, thus yielding a new set of singular values, $\Delta_{ux}$, and new sets of singular vectors, $P_{ux}$ and $Q'_{ux}$. Again, the data can have features enhanced or suppressed by modifying the singular vectors and/or singular values. The resulting singular values and singular vectors are provided to a subspace expansion module 66 where the singular values and singular vectors are expanded back into one or more full, two-dimensional images for display on monitor 34. When multiple sets are provided, the image can be displayed in three dimensions.

Referring to FIGS. 8(a)-8(c) and 9(a)-9(c), different forms of matrix analysis can be used correlate the images. Referring to FIGS. 8(a)-8(c), after a first ultrasound image U has been decomposed into singular vectors and singular values, a second mammographic image X is pre-multiplied by the left singular vectors $P'_u$ of ultrasound image U to determine the patterns of correlation $Q'_{ux}$ between U and X. Mammographic image X is then post-multiplied by right singular vectors $Q_u$ of the ultrasound image U to determine the patterns of correlation $P_{ux}$ between U and X. The singular vectors $P_{ux}$ are row-normalized, and an enhanced data matrix $X_{ux}$ is determined by multiplying the normalized $P_{ux}$ and $Q'_{ux}$.

Referring to FIGS. 9(a)-9(c), in another embodiment, the correlation between images U and X is determined by post-multiplying singular vectors $P_u$ by singular vectors $P_x$ to produce a correlation matrix $C_{ux}$. Next, singular vectors $P_x$ are post-multiplied by correlation matrix $C_{ux}$ to determine $P_{ux}$. A similar process is performed to derive $Q'_{ux}$. An enhanced matrix $X_{ux}$ is then determined through the matrix product $X_{ux}=P_{ux}Q'_{ux}$.

The system of the present invention is not limited to correlating one two-dimensional set of data and one three-dimensional data set. Rather, the system can correlate more data sets having any number of dimensions. Referring to FIG. 10, for example, in another embodiment of the data fusion function, the singular vectors and singular values of three different images X, Y, and Z are concatenated together to form a single, two-dimensional matrix 88. The concatenated matrix is decomposed into its singular values $\Delta_{xyz}$ and singular vectors $P_{xyz}$ and $Q'_{xyz}$. Based on analysis of the resulting singular values in $\Delta_{xyz}$ or the singular vectors, a subset of the singular values and singular vectors may be selected and/or weighted to represent intercorrelations between X, Y, and Z.

Referring to FIG. 11, in yet another embodiment for intercorrelating data, such as ultrasound data and mammographic data, each separate level 90 of ultrasound data 91 is correlated with the mammographic data 92 using techniques described above, and the resulting data is displayed as part of a three-dimensional image.

Figure 12:
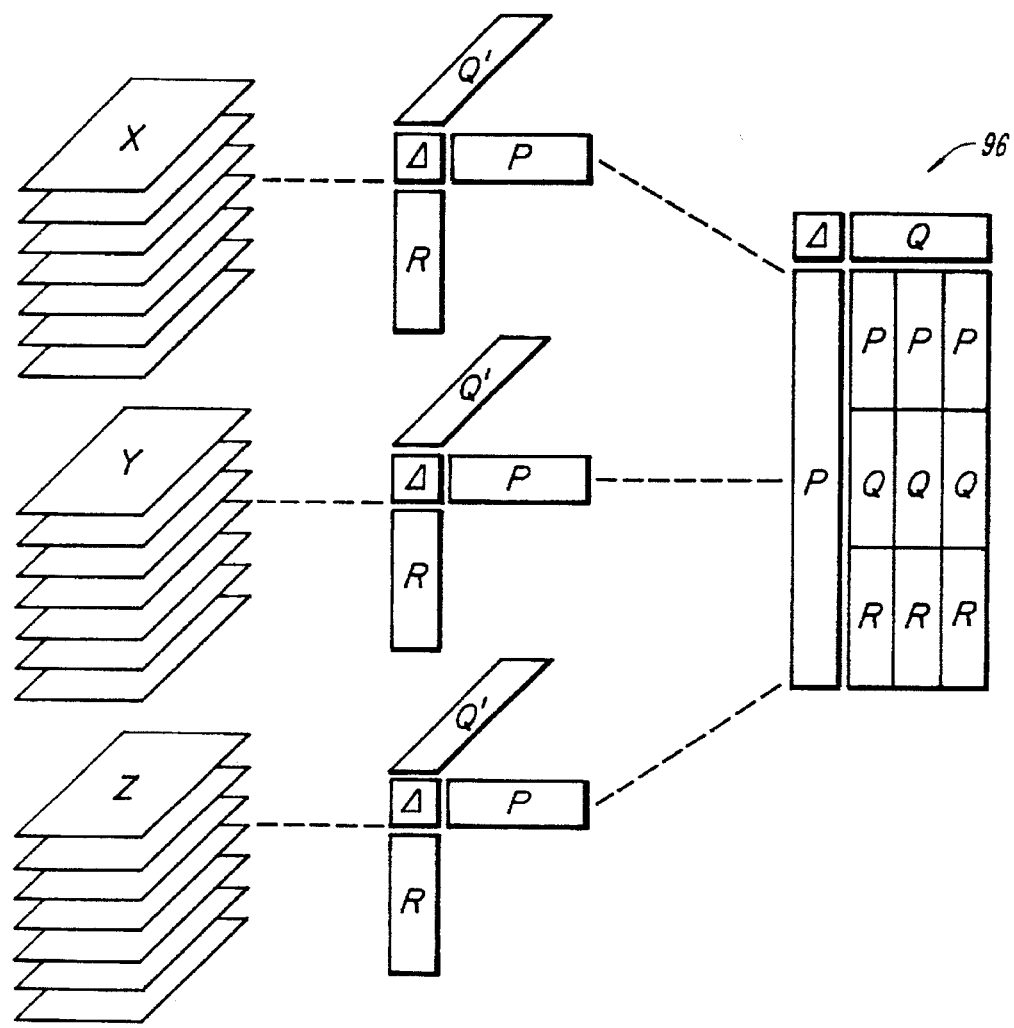

Referring to FIG. 12, in still another embodiment of the system for intercorrelating data, the singular vectors resulting from SVD of three-dimensional images X, Y, and Z are concatenated together to form a single, two-dimensional matrix 96. The concatenated matrix is decomposed into its singular values $\Delta_{xyz}$ and singular vectors $P_{xyz}$ and $Q'_{xyz}$. Based on analysis of the resulting singular values in $\Delta_{xyz}$ or the singular vectors, a subset of singular values and singular vectors may be selected and/or weighted to represent intercorrelations between X, Y, and Z.

Figure 13:
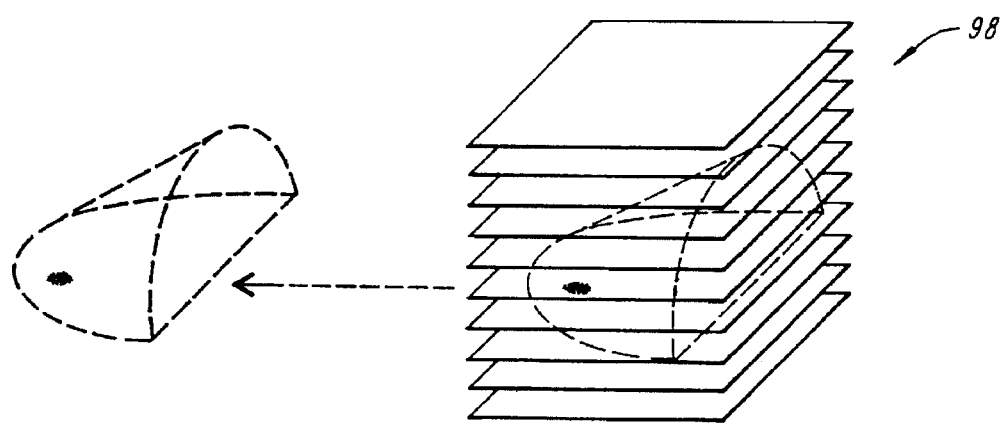
FIG. 13 illustrates a three-dimensional display of three-dimensional data constructed from two-dimensional data.

Referring again to FIG. 2, after the data is correlated, enhanced, and expanded, it is to provided to a display for visualization and analysis. Referring to FIG. 13, the three-dimensional data 98 may be displayed in layers which correspond to the levels of the ultrasound images. These layers may be viewed individually, or in sequence. Once in three-dimensional form, the data may be sliced at different angles and viewed in layers at difference orientations. In addition, the data may be thresholded, or otherwise modified to generate a transparent image of features within the breast. Additional data, such as from doppler analysis, may also be displayed as colors within the three-dimensional data.

While the foregoing invention has been described with reference to a preferred embodiment, it should be understood that various modifications and alterations will occur to those skilled in the art. Such modifications and alterations are intended to fall within the scope of the appended claims. For example, the system of the invention can be implemented with other data, including RF data, seismic data, communication data, as well as other medical imaging data. While the registration module and function has been described as following enhancements, data registration may instead be performed prior to the initial data enhancement function. While the enhancer has been described in terms of separate modules, all or some of these modules may be combined in a single piece of hardware and/or portions of software.

I claim:

1. A method for imaging a tissue region in a patient, the method including the steps of:

receiving a first set of imaging data of the tissue region from a first imaging source;

receiving a second set of imaging data of the tissue region from a second imaging source, the second imaging source being of a type that is different from the first imaging source; and concatenating, compressing, and enhancing the first and second sets of imaging data to produce a third single resulting set of enhanced data representing the tissue region.

2. The method of claim 1, wherein receiving the first set of imaging data includes receiving a two-dimensional representation of mammographic data.

3. The method of claim 1, wherein receiving the second set of imaging data includes receiving multiple sets of two-dimensional representations of ultrasound data.

4. The method of claim 2, wherein receiving the second set of imaging data includes receiving multiple sets of two-dimensional representations of ultrasound data.

5. The method of claim 1, wherein the step of concatenating, compressing, and enhancing step includes the substeps of:

decomposing the first set of imaging data into a first decomposed data set including singular values and singular vectors;

decomposing the second set of imaging data into a second decomposed data set including singular values and singular vectors;

concatenating the first decomposed data set and the second decomposed data set into a combined data set;

decomposing the combined data set to form an intermediate, compressed data set of singular values and singular vectors;

enhancing selected patterns of the intermediate, compressed set by altering the singular values and/or singular vectors to enhance desired features; and expanding the enhanced intermediate, compressed data set to form a third enhanced data set.

6. The method of claim 5, wherein the step of receiving the first set of imaging data and the substeps of decomposing the first set of imaging include receiving a number of two-dimensional sets of data, averaging the two-dimensional sets, and decomposing the averaged two-dimensional sets.

7. The method of claim 5, wherein receiving the first set of imaging data includes receiving a two-dimensional representation of mammographic data.

8. The method of claim 7, wherein receiving the second set of imaging data includes receiving multiple sets of two-dimensional representations of ultrasound data.

9. The method of claim 8, wherein the enhancing step includes enhancing one of the first and second sets of data by altering the singular values and/or vectors.

10. The method of claim 1, wherein the steps of receiving the first set of imaging data and the second set of imaging data each include receiving data from an imaging source selected from a group consisting of ultrasound imaging, including pulsed and CW doppler, magnetic resonance imaging (MRI), MRI spectroscopy (MRIS), fluoroscopy, angiography, computer tomography (CT), ultrafast computer tomography (UFCT), imaging based on electrocadiography (EKG), imaging based on electroencephalography (EEG), positron emission tomography (PET), single positron emission tomography (SPECT), and other techniques, radiological or otherwise, that produce mammography imaging and/or imaging of tissue.

11. The method of claim 1, wherein the first and second sets of imaging data are representative of three-dimensional image.

12. The method of claim 1, wherein the method further includes the step of altering the first and second sets of imaging to enhance a desired feature.

13. A system for imaging a tissue region in a patient, the system including:

means for receiving a first set of imaging data of the tissue region from a first imaging source;

means for receiving a second set of imaging data of the tissue region from a second imaging source, the second imaging source being of a type that is different from the first imaging source; and means for concatenating, compressing, and enhancing the first and second sets of imaging data to produce a third resulting set of data representing the tissue region.

14. A system for imaging a tissue region in a patient, the system including:

means for receiving a first set of imaging data of the tissue region from a first imaging source;

means for receiving a second set of imaging data of the tissue region from a second imaging source, the second imaging source being of a type that is different from the first imaging source; and means for concatenating, compressing, and enhancing the first and second sets of imaging data to produce a resulting third set of data representing the tissue region; and a display for displaying an image based on the third resulting set of data.

* * * * *